US011439519B2

(12) United States Patent
Xiong et al.

(10) Patent No.: US 11,439,519 B2
(45) Date of Patent: Sep. 13, 2022

(54) UNDER-DRIVEN PROSTHETIC HAND WITH SELF-ADAPTIVE GRASPING FUNCTION

(71) Applicant: HUAZHONG UNIVERSITY OF SCIENCE AND TECHNOLOGY, Hubei (CN)

(72) Inventors: Cai-Hua Xiong, Hubei (CN); Chuang Liu, Hubei (CN); Bai-Yang Sun, Hubei (CN); Zhi-Liang Xie, Hubei (CN); Tao Duan, Hubei (CN)

(73) Assignee: HUAZHONG UNIVERSITY OF SCIENCE AND TECHNOLOGY, Hubei (CN)

( * ) Notice: Subject to any disclaimer, the term of this patent is extended or adjusted under 35 U.S.C. 154(b) by 142 days.

(21) Appl. No.: 16/985,244

(22) Filed: Aug. 5, 2020

(65) Prior Publication Data
US 2021/0353437 A1 Nov. 18, 2021

(30) Foreign Application Priority Data

May 15, 2020 (CN) .......................... 202010413926.9

(51) Int. Cl.
*A61F 2/58* (2006.01)
*A61F 2/50* (2006.01)
*A61F 2/68* (2006.01)

(52) U.S. Cl.
CPC ...... *A61F 2/586* (2013.01); *A61F 2002/5003* (2013.01); *A61F 2002/5083* (2013.01);
(Continued)

(58) Field of Classification Search
CPC .............. A61F 2/586; A61F 2002/5003; A61F 2002/5083; A61F 2002/5084; A61F 2002/587; A61F 2002/6836
See application file for complete search history.

(56) References Cited

U.S. PATENT DOCUMENTS

| 1,474,301 A * | 11/1923 | Therrien ................. A61F 2/588 |
| | | 623/57 |
| 2008/0109084 A1* | 5/2008 | Maitland .................. A61F 2/68 |
| | | 623/21.11 |

(Continued)

FOREIGN PATENT DOCUMENTS

| CN | 103565562 | 2/2014 |
| CN | 104382674 | 3/2015 |
| WO | WO-2020173219 A1 * | 9/2020 |

*Primary Examiner* — Yashita Sharma
*Assistant Examiner* — Maximilian Tobias Spencer
(74) *Attorney, Agent, or Firm* — JCIP Global Inc.

(57) ABSTRACT

An under-driven prosthetic hand with a self-adaptive grasping function is provided, which belongs to the field of medical equipment. The prosthetic hand simultaneously controls four fingers to implement bending and stretching movements by a first motor through structural designs of a prosthetic hand body, a finger transmission module, an inter-finger transmission module, and a thumb driving module, and limits the transmission torque between the motor and screws using a damping shaft and in cooperation with the telescopic characteristic of a telescopic component. On the one hand, mechanical damage to the prosthetic hand structure due to excessive torque outputted by the motor can be prevented. On the other hand, the self-adaptive grasping function of the prosthetic hand can be implemented. The disclosure can also effectively solve issues such as excessive volume or mass of the prosthetic hand, complicated control system, and low operation precision.

15 Claims, 4 Drawing Sheets

(52) U.S. Cl.
CPC . *A61F 2002/5084* (2013.01); *A61F 2002/587* (2013.01); *A61F 2002/6836* (2013.01)

(56) References Cited

U.S. PATENT DOCUMENTS

2020/0384637 A1* 12/2020 Asada ................... B25J 5/007
2021/0128323 A1* 5/2021 Traverso ................ A61F 2/58

* cited by examiner

UNDER-DRIVEN PROSTHETIC HAND WITH SELF-ADAPTIVE GRASPING FUNCTION

CROSS-REFERENCE TO RELATED APPLICATION

This application claims the priority benefit of China application serial no. 202010413926.9, filed on May 15, 2020. The entirety of the above-mentioned patent application is hereby incorporated by reference herein and made a part of this specification.

BACKGROUND

Technical Field

The disclosure relates to the field of medical equipment, and more specifically to an under-driven prosthetic hand with a self-adaptive grasping function.

Description of Related Art

Since the emergence of humans, hands have always been an indispensable part of human evolution. Hands play an extremely important role in the production life of humans. Also, dexterous hands are also one of the most important features to distinguish humans as superior primates from other inferior animals. The important feature of the hands is that the hands have great dexterity and can complete various complex tasks for humans, while the damage or lack of hands will bring great inconvenience to the lives of people. Whether in domestic or foreign countries, there are a large number of cases of hand amputation patients, and with the passage of time, the number of hand amputation patients is also increasing year by year. Therefore, the development of prosthetic hands with personified functions, personified appearances, and convenience of use has extremely important scientific significance and social value.

At present, prosthetic hands generally have some issues, such as single functionality, non-personified movements, complicated control systems, and excessive volume or mass. An under-driven prosthetic hand is proposed in the Chinese Patent No. CN201310335089.2. Although the hand can solve the issue of excessive volume or mass to a certain extent, the structure of the entire prosthetic hand is complicated and the control system is complicated, resulting in the manipulation accuracy of the entire prosthetic arm to be not high. An under-driven prosthetic hand is proposed in the Chinese Patent No. CN201410559465.0, which can reproduce the rich grasping function of the hand to a certain extent, and has characteristics such as compact structure, and further reduction in volume and weight. However, the transmission mechanism of the palm part is complicated and occupies a large volume, resulting in the volume of the entire prosthetic hand to still be large, which is inconvenient for the patient to carry. Although the two types of under-driven prosthetic hands have solved the issue of excessive volume or mass to a certain extent, for the actual use of the patient, the volume or mass, manipulation accuracy, operation dexterity, etc. thereof still need relatively great improvement and progress.

SUMMARY

In response to the defects or improvement requirements of the prior art, the disclosure provides an under-driven prosthetic hand with a self-adaptive grasping function. The objective thereof is to complete the grasping task of multiple objects through the structural improvement of the finger transmission mechanism, inter-finger driving mechanism, and thumb driving mechanism, and adopting a single motor to control the bending and stretching movements of the four fingers of the prosthetic hand while the thumb is separately controlled by another motor. The disclosure has a self-adaptive grasping function while reproducing the grasping function of the hand, which can self-adaptively adjust the grasping state according to the shape of the grasping object, implement the personified envelope grasping of the grasping object, and effectively solve issues such as excessive volume or mass of the prosthetic hand, complicated control system, and low operation precision while having the self-adaptive grasping function.

In order to achieve the above objective, according to an aspect of the disclosure, an under-driven prosthetic hand with a self-adaptive grasping function is provided, including a prosthetic hand body, a finger transmission module, an inter-finger transmission module, and a thumb driving module.

The prosthetic hand body includes a palm and five fingers, and each finger is respectively pulled to be bent by respective first driving ropes and pulled to be stretched by respective second driving ropes.

The inter-finger transmission module is disposed inside the palm and includes an inter-finger driving mechanism, an inter-finger transmission mechanism, and an inter-finger proportional transmission mechanism.

The inter-finger driving mechanism includes a first motor and a first driving gear fixed onto an output shaft of the first motor, and the first motor is fixed onto to the palm.

The inter-finger transmission mechanism includes a first inter-finger transmission mechanism and a second inter-finger transmission mechanism distributed on both sides of the first motor. The first inter-finger transmission mechanism includes a first screw nut, a first polished rod, a first sliding block, and a first transmission gear, a first damping shaft, a first screw connector, and a first screw sequentially connected along a direction from a palm root to a metacarpophalangeal end. The first screw nut is disposed on the first screw, and the first sliding block is fixed onto the first screw nut and slides along the first polished rod.

The second inter-finger transmission mechanism includes a second screw nut, a second polished rod, a second sliding block, and a second transmission gear, a second damping shaft, a second screw connector, and a second screw sequentially connected along the direction from the palm root to the metacarpophalangeal end. The second screw nut is disposed on the second screw, and the second sliding block is fixed onto the second screw nut and slides along the second polished rod.

The first screw, the second screw, the first polished rod, and the second polished rod are parallel to each other and are all fixed onto the palm.

The proportional transmission mechanism includes a telescopic component and four third pulleys. The telescopic component is disposed with four fixed points arranged in a straight line, which one-to-one correspondingly fix the respective first driving ropes of the remaining four fingers other than the thumb, or one-to-one correspondingly fix the respective second driving ropes of the remaining four fingers other than the thumb. A distance between any two adjacent fixed points is telescopic. The telescopic component is pivotally connected onto the first sliding block and the second sliding block respectively through two pins. The four third pulleys are disposed near the palm root and one-to-one correspond to the remaining four fingers other than the thumb. After the respective driving ropes of the remaining four fingers other than the thumb are wound around the corresponding third pulleys, the driving ropes are divided into the first driving ropes and the second driving ropes by the third pulleys.

The thumb is independently driven by the thumb driving module. The thumb driving module includes a second motor fixed onto the palm and a thumb bending pulley fixed onto an output shaft of the second motor. After the driving ropes of the thumb are wound around the thumb bending pulley, the driving ropes are divided into a first driving rope and a second driving rope by the thumb bending pulley.

Further, the five fingers are respectively the thumb, index finger, middle finger, ring finger, and little finger, and each includes a metacarpophalangeal joint component, a proximal joint component, a middle segment, and a distal segment.

The metacarpophalangeal joint component includes a metacarpophalangeal segment, a metacarpophalangeal joint shaft, and a first pulley with the metacarpophalangeal joint shaft as a rotating shaft.

The proximal joint component includes a proximal segment, a proximal joint shaft, and a second pulley with the proximal joint shaft as a rotating shaft. The metacarpophalangeal joint shaft connects the metacarpophalangeal segment and the proximal segment. The proximal joint shaft connects the proximal segment and the middle segment. The distal segment and the middle segment are connected at a preset bending angle.

A finger transmission module is disposed inside each of the five fingers. The finger transmission module includes a first driving rope, a second driving rope, and a first tensioning rope, a proximal segment coupling spring, and a second tensioning rope sequentially connected in series.

The first driving rope and the second driving rope are arranged by pulling. One ends of the first driving rope and the second driving rope are fixed onto the end of the middle segment or the distal segment, and the other ends are introduced into the palm after being wound around each of the second pulley and the first pulley by one round.

The first tensioning rope and the second tensioning rope are respectively wound around the metacarpophalangeal joint shaft and the proximal joint shaft.

Further, a first installation plate is disposed near the palm root of the palm, and the four third pulleys are fixed onto the first installation plate.

The telescopic component is a scissoring proportional mechanism, including a first transmission pin, a second transmission pin, a third transmission pin, a fourth transmission pin, a first link, a second link, a third link, a fourth link, a fifth link, a sixth link, a seventh link, and an eighth link.

The first link, the fourth link, the fifth link, and the eighth link are pivotally connected in sequence. The second link, the third link, the sixth link, and the seventh link are pivotally connected in sequence. The first link and the second link are pivotally connected through the first transmission pin. The seventh link and the eighth link are pivotally connected through the fourth transmission pin. The third link and the fourth link intersect and are pivotally connected through the second transmission pin at the intersection point. The fifth link and the sixth link intersect and are pivotally connected through the third transmission pin at the intersection point.

The first transmission pin to the fourth transmission pin are the four fixed points, and two of the first transmission pin to the fourth transmission pin are respectively fixed onto the first sliding block and the second sliding block, so that the scissoring proportional mechanism is pivotally connected to the first sliding block and the second sliding block respectively.

Further, the thumb driving module further includes a driving rope guide, a thumb support, a thumb side-swing damping shaft, and a thumb connector connected to the thumb side-swing damping shaft. The driving rope guide and the thumb support are fixed onto the first installation plate. One end of the thumb side-swing damping shaft is fixed to the thumb support, and the other end is fixed to the thumb connector. The thumb is installed onto the thumb connector.

Further, the first transmission pin to the fourth transmission pin are respectively limited to the respective corresponding pivotally connected links using circlips.

Further, linear bearings correspondingly cooperating with the first polished rod and the second polished rod are respectively installed in the first sliding block and the second sliding block.

Further, the metacarpophalangeal segments and the middle segments of respective fingers are all respectively provided with positioning pins to prevent the fingers from bending toward the opposite direction, and to limit the maximum bending angle of each segment toward the palm to 90 degrees.

Generally speaking, compared with the prior art, the technical solution conceived by the disclosure mainly have the following technical advantages:

1. The inter-finger transmission module in the prosthetic hand of the disclosure is controlled by the first motor to simultaneously control the four fingers to implement bending and stretching movements. Fewer motors can further simplify the palm structure and further reduce the volume and mass of the prosthetic hand.

In addition, the damping shaft adopted in the transmission mechanism can limit the transmission torque between the motor and the screw. When the rotational torque is greater than the internal resistance of the damping shaft, both ends of the damping shaft rotate relative to each other to discharge the force, which can prevent the prosthetic hand structure from being mechanically damaged due to excessive torque outputted by the motor, and also realize the self-adaptive grasping function of the prosthetic hand. When the movement of one or more fingers is blocked, both ends of the damping shaft correspondingly rotate relative to each other, which will not cause the first motor to be mechanically locked. The first motor may still rotate normally and continue to drive the remaining fingers to move, so as to implement the self-adaptive envelope grasping movement of an object.

Due to the telescopic characteristic of the telescopic component, during the process where the movement of one or some fingers are blocked while the remaining fingers continue to move, the telescopic component may be elongated and tilted to prevent causing the first motor to be mechanically locked or the driving rope to be stuck.

2. The disclosure uses pulleys as the main constituting components in the finger, finger internal transmission mechanisms adopt wire ropes and springs as transmission mediums, while finger components are further reduced, so that the finger can accurately and effectively complete the bending and straightening movements. In particular, the design of double joints is adopted to further reduce the degree of complexity of the finger structure, which further reduces the volume and mass of the prosthetic finger. At the same time, the preset bending angle adopted by the distal joints may also ensure the fingers to achieve the personified grasping movement, so as to implement the effective envelope grasping of multiple objects.

3. The preferred scissoring proportional mechanism of the disclosure has the telescopic function while achieving a more stable synchronous transmission with a thinner structure than a traditional telescopic rod, so as to have good stability while saving space to implement a compact design. In addition, the four pins can also be ensured to always be in a straight line, so as to implement a fixed proportional transmission of the four points.

4. In the prosthetic hand of the disclosure, the side-swing movement of the thumb is passively implemented through the obstructive action of the object being grasped or the action of other external forces using the damping characteristics of the damping shaft. Under the action of the damping shaft, the thumb may be kept at any swing angle, and the direction of the thumb may be changed to adapt to the grasping of different shapes and sizes of objects, so as to expand the grasping range of the prosthetic hand, and enhance the grasping ability of the prosthetic hand.

5. The circlips can effectively prevent the pins from falling off when pulling the driving ropes.

6. The linear bearings can effectively reduce the magnitude of the frictional force generated during the movement process of the sliding blocks with the polished rods.

7. The positioning pins can play the role of mechanical limitation. On the one hand, the positioning pins prevent the fingers from bending toward the opposite direction. On the other hand, the positioning pins ensure that the maximum bending of each segment toward the palm is 90 degrees to ensure the movement range of the fingers.

BRIEF DESCRIPTION OF THE DRAWINGS

In all the drawings, the same reference numeral is used to denote the same element or structure.

DETAILED DESCRIPTION OF DISCLOSED EMBODIMENTS

In order to make the objective, technical solution, and advantages of the disclosure clearer, the disclosure will be further described in detail below with reference to the drawings and embodiments. It should be understood that the specific embodiments described herein are only used to explain the disclosure, and are not intended to limit the disclosure. In addition, the technical features involved in the various embodiments of the disclosure described below may be combined with each other as long as there is no conflict with each other.

Figure 1:
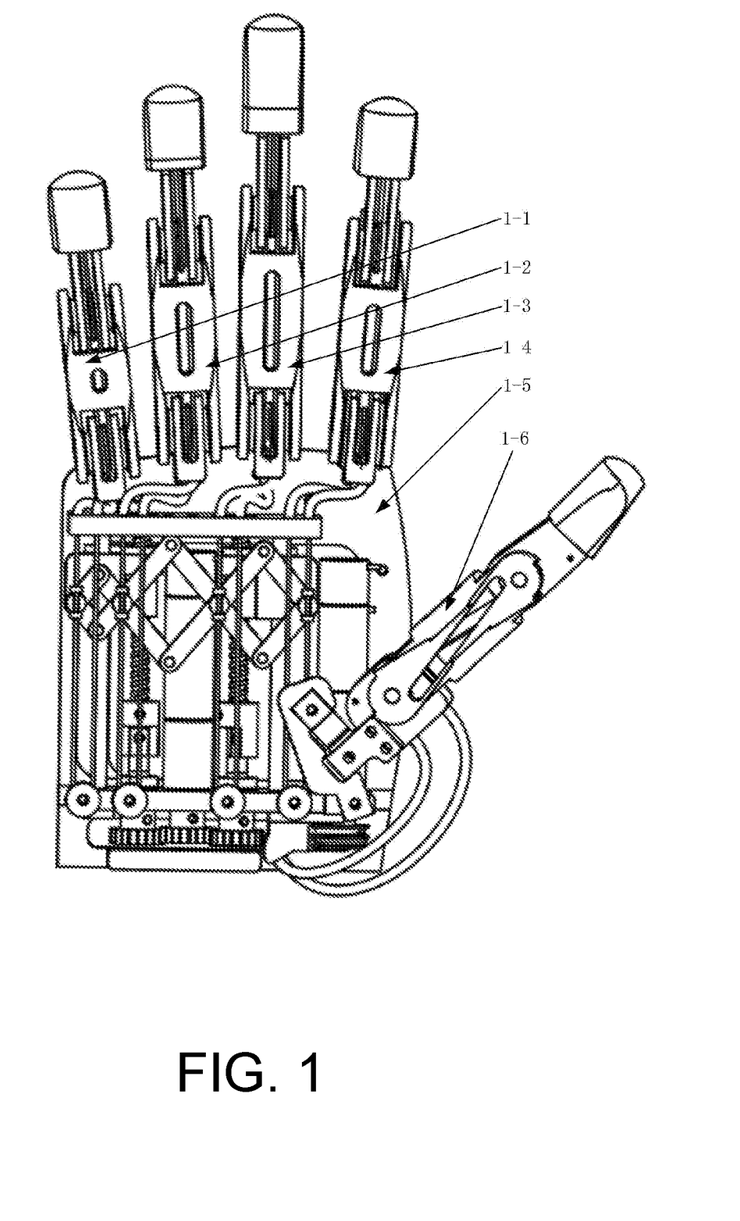
FIG. 1 is a schematic view of an overall structure of a prosthetic hand device constructed according to the disclosure.

FIG. 1 is a schematic view of an overall structure of an under-driven prosthetic hand with a self-adaptive grasping function according to a preferred embodiment of the disclosure. As shown in FIG. 1, the prosthetic hand mainly includes a prosthetic hand body, a finger transmission module, an inter-finger transmission module, and a thumb driving module, wherein the structures of the key components such as finger internal transmission mechanisms, the inter-finger driving module, and the thumb driving module are designed to be improved, so that two power sources may be adopted to accurately control five fingers of the prosthetic hand with a total of 10 degrees of freedom, so as to complete the operation function of self-adaptive envelope grasping of multiple objects.

Figure 2:
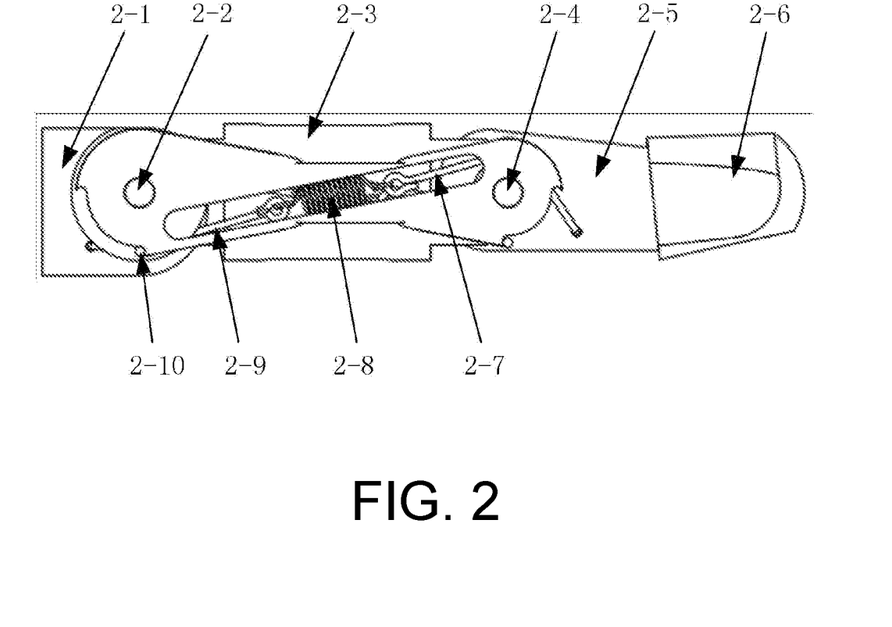
FIG. 2 is a front view of a structure of a two joint under-driven finger shown in FIG. 1.
Figure 3:
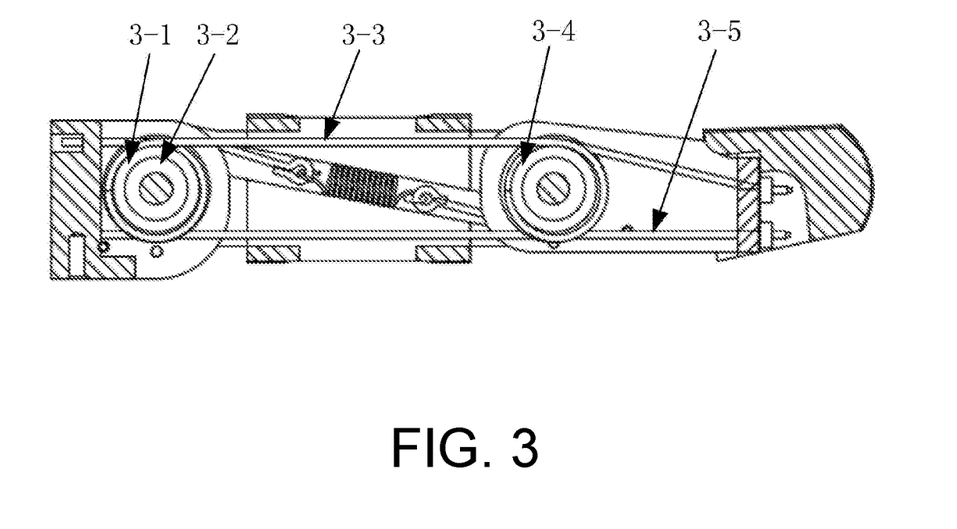
FIG. 3 is a cross-sectional view of the structure of the two-joint under-driven finger shown in FIG. 1.

Specifically, referring to FIG. 1, FIG. 2, and FIG. 3, the prosthetic hand body is composed of a palm 1-5 and a thumb 1-6, an index finger 1-4, a middle finger 1-3, a ring finger 1-2, and a little finger 1-1 having the same structure. Each finger respectively includes four parts, a metacarpophalangeal joint component, a proximal joint component, a middle segment 2-5, and a distal segment 2-6.

The metacarpophalangeal joint component includes a metacarpophalangeal segment 2-1, a metacarpophalangeal joint shaft 2-2 laterally disposed near the center position of the metacarpophalangeal segment, and a first pulley 3-1 centrally disposed on the metacarpophalangeal joint shaft 2-2 along the axial direction of the finger. The proximal joint component includes a proximal segment 2-3, a proximal joint shaft 2-4 laterally disposed at the distal position of the proximal segment 2-3, and a second pulley 3-4 centrally disposed on the proximal joint shaft along the axial direction of the finger. The proximal segment 2-3 has a cylindrical structure, and is respectively connected to the metacarpophalangeal segment and the proximal segment. The middle segment 2-5 has a cubic structure, the distal segment 2-6 is in the shape of a human finger, and the two are connected together to form an overall bending design. The bending angle replaces the simplified and omitted the metacarpophalangeal distal phalanx joint angle of the hand, which indicates that the metacarpophalangeal distal phalanx joint of the hand has a certain bending angle, so as to implement the personified envelope grasping movement. Both ends of the metacarpophalangeal joint shaft 2-2 and the proximal joint shaft 2-4 are fixed by bearings, and both may rotate around the bearings. The proximal segment 2-3 and the middle segment 2-5 may be bent around the shafts.

The metacarpophalangeal joint shaft 2-2 connects the metacarpophalangeal segment 2-1 and the proximal segment 2-3, and the proximal joint shaft 2-4 connects the proximal segment 2-3 and the middle segment 2-5 to ensure a certain segment may rotate relative to an adjacent segment. As a preferred embodiment, the pulleys at each joint are all symmetrically arranged at the center.

As a further preferred embodiment of the disclosure, the finger internal transmission mechanisms are respectively disposed inside the five fingers and are symmetrically arranged on both sides of the fingers. Each includes symmetrically arranged first driving rope 3-3 and second driving rope 3-5 wound around the first pulley 3-1 and the second pulley 3-4, a first tensioning rope 2-9 and a second tensioning rope 2-7 symmetrically arranged at both sides of the finger, located between the metacarpophalangeal segment and the proximal segment, and are respectively wound around the ends of the cylindrical structure at the metacarpophalangeal segment 2-1 and the middle segment 2-5, and a proximal segment coupling spring 2-8 disposed between the first pulley 3-1 and the second pulley 3-4 to connect the two tensioning ropes. The first tensioning rope 2-9 is wound around one end of the cylindrical structure at the metacarpophalangeal segment 2-1 with one end connected to the proximal segment coupling spring 2-8, and the other end fixed onto the metacarpophalangeal segment 2-1. The second tensioning rope 2-7 is wound around one end of the cylindrical structure at the middle segment 2-5 with one end connected to the proximal segment coupling spring 2-8, and the other end fixed onto the middle segment 2-5. The two driving ropes 3-3 and 3-5 adopt the manner of pulling to respectively drive the fingers to bend and stretch.

The coupling movement of the metacarpophalangeal segment and the proximal segment is implemented through the first tensioning rope 2-9 and the second tensioning rope 2-7 at both sides inside the finger and the proximal segment coupling spring 2-8. The specific process is that when the first driving rope 3-3 is pulled, the metacarpophalangeal segment 2-1 and the proximal segment 2-3 are bent at the same time. At this time, since the first tensioning rope 2-9, the second tensioning rope 2-7, and the proximal segment coupling spring 2-8 are combined to connect the metacarpophalangeal segment 2-1 and the middle segment 2-5, the bending angles of the metacarpophalangeal joint and the proximal joint are affected by the radius of the cylindrical structure on the segments wound by the first tensioning rope 2-9 and the second tensioning rope 2-7. The ratio of the bending angle is related to the ratio of the radius of the cylindrical structure. The resetting process is implemented by pulling the second driving rope 3-5, and the movement relationship of each joint is similar to the transmission relationship. The middle segment 2-5 and the distal segment 2-6 are connected at a fixed bending angle, which indicates that the distal joint angle of the prosthetic finger is at a fixed bending angle, so as to simplify the finger structure and reduce the finger volume and mass without reducing the grasping stability. On the contrary, the grasping stability is improved due to the reduction of transmission routine.

In addition, as shown in FIG. 2, for the prosthetic fingers, each metacarpophalangeal segment 2-1 and middle segment 2-5 is equipped with a positioning pin 2-10, which can play the role of mechanical limitation. On the one hand, the positioning pins prevent the fingers from bending toward the opposite direction. On the other hand, the positioning pins ensure that the maximum bending of each segment toward the palm is 90 degrees to ensure the movement range of the fingers. Preferably, a baffle plate with a 90-degree arc groove may be disposed on each metacarpophalangeal joint shaft 2-2 and proximal joint shaft 2-4 to cooperate with the positioning pin 2-10. The two baffle plates may be integrally formed to further increase the finger strength.

Figure 4:
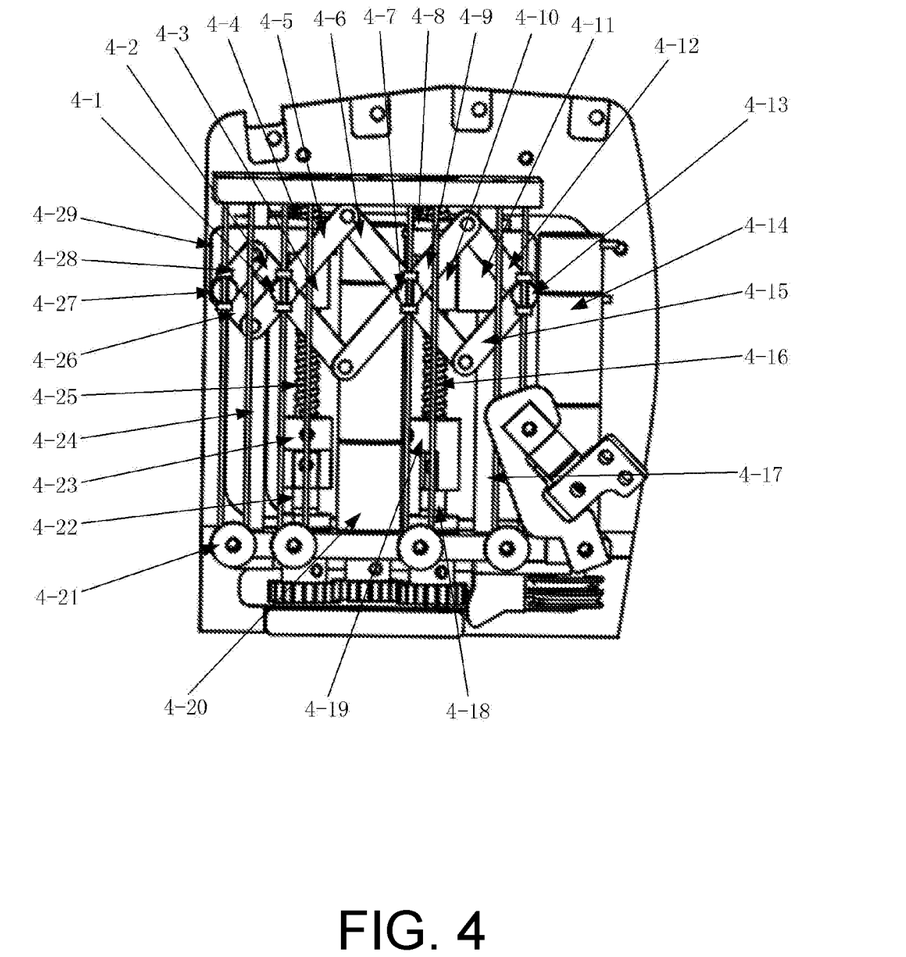
FIG. 4 is a front view of an overall structure of a finger transmission mechanism shown in FIG. 1.
Figure 5:
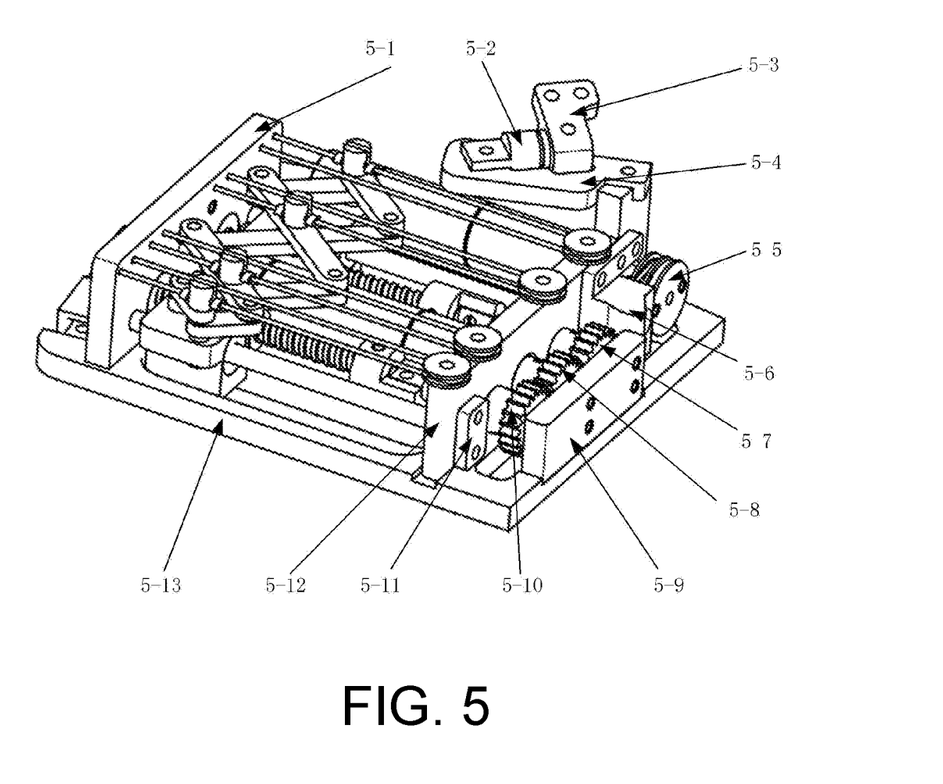
FIG. 5 is an axonometric view of the overall structure of the finger transmission mechanism shown in FIG. 1.

As the key invention of the disclosure, referring to FIG. 4 and FIG. 5, the inter-finger transmission module is disposed inside the palm, and mainly includes three parts, an inter-finger driving module, an inter-finger transmission module and an inter-finger movement distribution module.

The inter-finger driving module includes a first motor 4-20 and a first driving gear 5-8 fixed onto the first motor shaft. The first motor 4-20 is fixed onto an installation plate 5-12. The inter-finger transmission module is divided into two parts, a first inter-finger transmission mechanism and a second inter-finger transmission mechanism, which are symmetrically arranged on both sides of the first motor. The first inter-finger transmission mechanism includes a first transmission gear 5-10, a first damping shaft 4-22, a first damping shaft and screw connector 4-23, a first screw 4-25, a first screw nut 4-3, a first polished rod 4-24, and a first sliding block 4-29. The second inter-finger transmission mechanism and the first inter-finger transmission mechanism are symmetrically arranged. The screw and the polished rod are fixedly installed on the palm 1-5 through the first installation plate 5-12 and a second installation plate 5-1. Two ends of the damping shaft are respectively connected to the corresponding screw and transmission gear.

The core component of the proportional transmission mechanism is the telescopic component, which may be designed by adopting a traditional telescopic rod structure. Preferably, the embodiment provides a scissoring proportional mechanism to implement the telescopic function. The proportional transmission mechanism of the embodiment mainly includes a first transmission pin 4-27, a second transmission pin 4-1, a third transmission pin 4-7, a fourth transmission pin 4-13, a first link 4-26, a second link 4-28, a third link 4-2, a fourth link 4-5, a fifth link 4-6, a sixth link 4-9, a seventh link 4-12, an eighth link 4-15, and four third pulleys 4-21 fixed onto the first installation plate 5-12 with the same structure. The eight links are intersected and connected to form the scissoring proportional mechanism. One end of each transmission pin is respectively connected to the driving ropes of the index finger, the middle finger, the ring finger, and the little finger, thereby driving each finger to perform a bending movement. The other end is respectively used as a pivoting rod of the corresponding link. The first transmission pin 4-27 and the fourth transmission pin 4-13 are respectively consolidated with the first sliding block 4-29 and a second sliding block 4-11.

For the first inter-finger transmission mechanism, the first screw nut 4-3 is sleeved on the first screw 4-25 and is embedded in a groove at one end of the first sliding block 4-29 to be fixed through a first pressure plate 4-4. The first sliding block 4-29 is embedded in the linear bearing and is sleeved on the first polished rod 4-24, and may slide back and forth on the first polished rod 4-24. The second inter-finger transmission mechanism and the first inter-finger transmission mechanism have the same structure, and are symmetrically arranged on the other side of the first motor 4-20.

Specifically, through the above design, when the first motor 4-20 is running, the driving torque is outputted through the first driving gear 5-8 to drive the first transmission gear 5-10 and the second transmission gear 5-7 to rotate, and then transmitted to the first screw 4-25 and the second screw 4-16 through the first damping shaft 4-22 and a second damping shaft 4-18 to drive the two screws to rotate. The rotation of the two screws respectively drive the first screw nut 4-3 and the second screw nut 4-10 to move up and down linearly.

Figure 6:
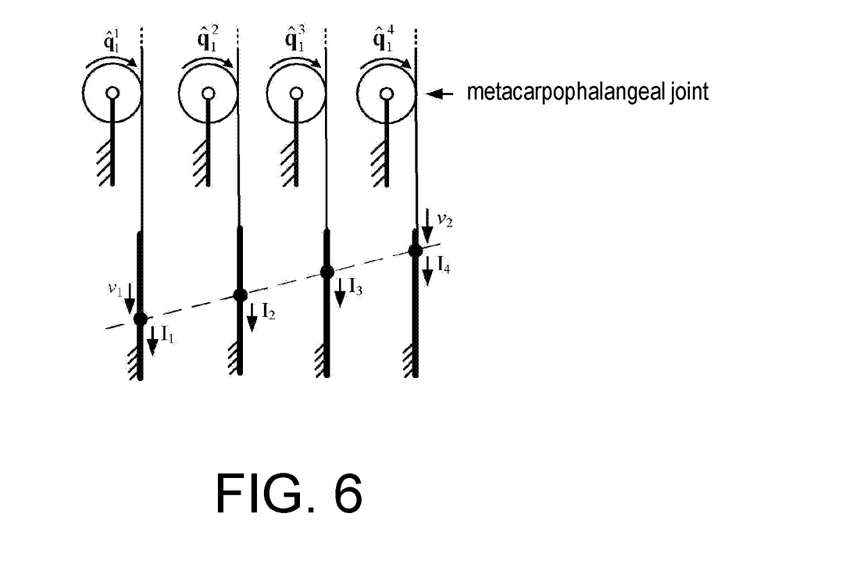
FIG. 6 is a proportional transmission principle diagram of a proportional transmission mechanism in FIG. 4, wherein: v1 and v2 are two inputs generated by rotation of a first motor; $I_1$ to $I_4$ are four outputs obtained through proportional transmission, corresponding to remaining four fingers other than a thumb; and $\hat{q}_1^1$ to $\hat{q}_1^4$ are rotational angles of metacarpophalangeal joints generated by four driving ropes pulling four first pulleys.

Since the first screw nut 4-3 and the second screw nut 4-10 are respectively consolidated with the first sliding block 4-29 and the second sliding block 4-11, the two sliding blocks and the two screw nuts move up and down linearly together. Since the first transmission pin 4-27 and the fourth transmission pin 4-13 are respectively consolidated onto the two sliding blocks, and the four transmission pins are all the pivot shafts of the scissoring proportional mechanism composed of the eight links (4-26, 4-28, 4-2, 4-5, 4-6, 4-9, 4-12, and 4-15), all the transmission pins may respectively move up and down linearly along with the two sliding blocks, thereby pulling the driving rope of each finger up and down to drive each finger to implement bending or stretching movement. Also, the movement of each transmission pin is in a fixed proportion, as shown in FIG. 6. Since the first driving rope 3-3 and the second driving rope 3-5 is each wound around the first pulley 3-1 by one round, the input force and output force generated on the first pulley 3-1 are collinear. Therefore, the thick lines representing the four output forces in FIG. 6 are collinear with the thin lines representing the driving ropes on the four corresponding pulleys. The driving rope pulling arrangement formed by adopting such routing method generates the most stable driving force, and the driving rope displacement is easier to be accurately controlled.

Preferably, in the embodiment, a sleeve tube is adopted for the transition between the finger root position of each finger and the palm, and the first driving rope 3-3 and the second driving rope 3-5 of each finger pass through the respective corresponding sleeve tubes, thereby fixing the path length in the transition zone and protecting the driving ropes to prevent the interference from the outside or each other during the working process.

When the movement of the sliding block on one side is blocked, the torque of the damping shaft will exceed the rated transmission torque to overcome the damping action, so that the two ends of the damping shaft will relatively slide to prevent the first motor 4-20 from being mechanically locked. The first motor 4-20 may continue to drive the sliding block on the other side. Using such principle, the self-adaptive envelope grasping function of the prosthetic hand may be implemented. Specifically, when the movement one or some of the remaining four fingers other than the thumb are blocked, the remaining fingers may continue to move until the sliding blocks on both sides are blocked at the same time (that is, all four fingers are blocked) to implement envelope grasping. Based on the principle, in fact, any two of the four transmission pins may be used to be respectively consolidated onto the two sliding blocks. However, in the embodiment, the transmission pins corresponding to the little finger 1-1 and the index finger 1-4 are consolidated onto the two sliding blocks, which is most suitable for the habitual movement of the hand, that is, the little finger or the index finger first contacts the object to be grasped, or the little finger and the index finger grasp at the same time.

As another key improvement of the disclosure, the thumb driving module is also disposed inside the palm, and mainly includes a second motor 4-14 fixed onto the installation plate 5-12, a thumb bending pulley 5-5 fixed onto the motor shaft, a driving rope guide 5-6 fixed onto the installation plate 5-12, a thumb support 5-4 fixed onto the installation plate 5-12, a thumb side-swing damping shaft 5-2, and a thumb connector 5-3 connected to the thumb side-swing damping shaft. One end of the thumb side-swing damping shaft 5-2 is connected to the thumb support 5-4, and the other end is connected to the thumb connector 5-3. The other end of the thumb connector 5-3 is connected to the thumb. A thumb driving line is symmetrically wound around the thumb bending pulley 5-5 to drive the thumb to implement bending movement. The thumb may swing around the central axis of the damping shaft 5-2 and may stay at any swing angle. The side-swing movement of the thumb of the prosthetic hand is passively implemented through the damping shaft 5-2. Preferably, the thumb support 5-4 in the embodiment is further provided with a yielding groove to yield the thumb connector 5-3, thereby further saving space, so that the structure is more compact.

In summary, the fingers are bent and stretched through rope pulling, so that multiple degrees of freedom may be changed through one input. Also, the first motor 4-20 is adopted to provide four outputs. Such method only adopts one motor to complete the driving of four fingers. At the same time, through the action of the damping shaft and the proportional transmission mechanism, the prosthetic hand only needs a motor to complete the self-adaptive envelope grasping function, has a certain amount of shape self-adaptive ability for complex objects, is easy to control, and is very suitable for the field of medical equipment. The thumb movement is independently driven through the second motor, and the side-swing movement is passively implemented, which further simplifies the structure of the prosthetic hand. At the same time, the controllability of the side-swing angle of the thumb (that is, self-positioning at any angle may be implemented through the action of the damping shaft) further increases the grasping range of the prosthetic hand, so as to enhance the grasping ability of the prosthetic hand.

It is easy for persons skilled in the art to understand that the above are only the preferred embodiments of the disclosure and is not intended to limit the disclosure. Any modification, equivalent replacement, improvement, etc. made within the spirit and principle of the disclosure should all be included in the protection scope of the disclosure.

What is claimed is:

1. An under-driven prosthetic hand with a self-adaptive grasping function, comprising a prosthetic hand body, a finger transmission module, an inter-finger transmission module, and a thumb driving module, wherein the prosthetic hand body comprises a palm and five fingers, and each of the fingers is respectively pulled to be bent by a first driving rope and pulled to be stretched by a second driving rope;

the inter-finger transmission module is disposed inside the palm and comprises an inter-finger driving mechanism, an inter-finger transmission mechanism, and an inter-finger proportional transmission mechanism, wherein the inter-finger driving mechanism comprises a first motor and a first driving gear fixed onto an output shaft of the first motor, and the first motor is fixed onto the palm;

the inter-finger transmission mechanism comprises a first inter-finger transmission mechanism and a second inter-finger transmission mechanism distributed on both sides of the first motor; the first inter-finger transmission mechanism comprises a first screw nut, a first polished rod, a first sliding block, and a first transmission gear, a first damping shaft, a first screw connector, and a first screw sequentially connected along a direction from a palm root to a metacarpophalangeal end; the first screw nut is disposed on the first screw, and the first sliding block is fixed onto the first screw nut and slides along the first polished rod;

the second inter-finger transmission mechanism comprises a second screw nut, a second polished rod, a second sliding block, and a second transmission gear, a second damping shaft, a second screw connector, and a second screw sequentially connected along the direction from the palm root to the metacarpophalangeal end; the second screw nut is disposed on the second screw, and the second sliding block is fixed onto the second screw nut and slides along the second polished rod;

the first screw, the second screw, the first polished rod, and the second polished rod are parallel to each other and are all fixed onto the palm; and the proportional transmission mechanism comprises a telescopic component and four third pulleys; the telescopic component is disposed with four fixed points arranged in a straight line, which one-to-one correspondingly fix the respective first driving ropes of remaining four fingers other than a thumb, or one-to-one correspondingly fix the respective second driving ropes of the remaining four fingers other than the thumb, and a distance between any two adjacent fixed points is telescopic; the telescopic component is pivotally connected to the first sliding block and the second sliding block respectively through two pins; the four third pulleys are disposed near the palm root and one-to-one correspond to the remaining four fingers other than the thumb; and after respective driving ropes of the remaining four fingers other than the thumb are wound around the corresponding third pulleys, the respective driving ropes are divided into the first driving ropes and the second driving ropes by the third pulleys; and the thumb is independently driven by the thumb driving module, the thumb driving module comprises a second motor fixed onto the palm and a thumb bending pulley fixed onto an output shaft of the second motor; and after a driving rope of the thumb is wound around the thumb bending pulley, the driving rope of the thumb is divided into the first drive rope and the second drive rope by the thumb bending pulley.

2. The under-driven prosthetic hand with a self-adaptive grasping function according to claim 1, wherein the five fingers are divided into the thumb, an index finger, a middle finger, a ring finger, and a little finger, respectively comprising a metacarpophalangeal joint component, a proximal joint component, a middle segment, and a distal segment, wherein the metacarpophalangeal joint component comprises a metacarpophalangeal segment, a metacarpophalangeal joint shaft, and a first pulley with the metacarpophalangeal joint shaft as a rotating shaft;

the proximal joint component comprises a proximal segment, a proximal joint shaft, and a second pulley with the proximal joint shaft as a rotating shaft; the metacarpophalangeal joint shaft connects the metacarpophalangeal segment and the proximal segment, and the proximal joint shaft connects the proximal segment and the middle segment; and the distal segment and the middle segment are connected at a preset bending angle;

the finger transmission module is disposed inside each of the five fingers, the finger transmission module comprises the first driving rope, the second driving rope, and a first tensioning rope, a proximal segment coupling spring, and a second tensioning rope sequentially connected in series;

the first driving rope and the second driving rope adopt a pulling arrangement; one ends of the first driving rope and the second driving rope are fixed onto an end of the middle segment or the distal segment, and other ends are introduced into the palm after being wound around each of the second pulley and the first pulley by one round; and the first tensioning rope and the second tensioning rope are respectively wound around the metacarpophalangeal joint shaft and the proximal joint shaft.

3. The under-driven prosthetic hand with a self-adaptive grasping function according to claim 2, wherein a first installation plate is disposed near the palm root of the palm, and the four third pulleys are fixed onto the first installation plate;

the telescopic component is a scissoring proportional mechanism, comprising a first transmission pin, a second transmission pin, a third transmission pin, a fourth transmission pin, a first link, a second link, a third link, a fourth link, a fifth link, a sixth link, a seventh link, and an eighth link;

the first link, the fourth link, the fifth link, and the eighth link are pivotally connected in sequence; the second link, the third link, the sixth link, and the seventh link are pivotally connected in sequence; the first link and the second link are pivotally connected through the first transmission pin; the seventh link and the eighth link are pivotally connected through the fourth transmission pin; the third link and the fourth link intersect and are pivotally connected through the second transmission pin at an intersection point; and the fifth link and the sixth link intersect and are pivotally connected through the third transmission pin at an intersection point; and the first transmission pin to the fourth transmission pin are the four fixed points, and two of the first transmission pin to the fourth transmission pin are respectively fixed onto the first sliding block and the second sliding block, so that the scissoring proportional mechanism is pivotally connected to the first sliding block and the second sliding block respectively.

4. The under-driven prosthetic hand with a self-adaptive grasping function according to claim 3, wherein the thumb driving module further comprises a driving rope guide, a thumb support, a thumb side-swing damping shaft, and a thumb connector connected to the thumb side-swing damping shaft; the driving rope guide and the thumb support are fixed onto the first installation plate; one end of the thumb side-swing damping shaft is fixed to the thumb support, and other end is fixed to the thumb connector; and the thumb is installed onto the thumb connector.

5. The under-driven prosthetic hand with a self-adaptive grasping function according to claim 3, wherein the first transmission pin to the fourth transmission pin are respectively limited to the respective corresponding pivotally connected links using circlips.

6. The under-driven prosthetic hand with a self-adaptive grasping function according to claim 1, wherein linear bearings correspondingly cooperating with the first polished rod and the second polished rod are respectively installed in the first sliding block and the second sliding block.

7. The under-driven prosthetic hand with a self-adaptive grasping function according to claim 2, wherein linear bearings correspondingly cooperating with the first polished rod and the second polished rod are respectively installed in the first sliding block and the second sliding block.

8. The under-driven prosthetic hand with a self-adaptive grasping function according to claim 3, wherein linear bearings correspondingly cooperating with the first polished rod and the second polished rod are respectively installed in the first sliding block and the second sliding block.

9. The under-driven prosthetic hand with a self-adaptive grasping function according to claim 4, wherein linear bearings correspondingly cooperating with the first polished rod and the second polished rod are respectively installed in the first sliding block and the second sliding block.

10. The under-driven prosthetic hand with a self-adaptive grasping function according to claim 5, wherein linear bearings correspondingly cooperating with the first polished rod and the second polished rod are respectively installed in the first sliding block and the second sliding block.

11. The under-driven prosthetic hand with a self-adaptive grasping function according to claim 1, wherein each of the metacarpophalangeal segments and the middle segments of the respective fingers are all respectively provided with positioning pins to prevent the fingers from bending toward an opposite direction, and to limit a maximum bending angle of each of the segments toward the palm to 90 degrees.

12. The under-driven prosthetic hand with a self-adaptive grasping function according to claim 2, wherein each of the metacarpophalangeal segments and the middle segments of the respective fingers are all respectively provided with positioning pins to prevent the fingers from bending toward an opposite direction, and to limit a maximum bending angle of each of the segments toward the palm to 90 degrees.

13. The under-driven prosthetic hand with a self-adaptive grasping function according to claim 3, wherein each of the metacarpophalangeal segments and the middle segments of the respective fingers are all respectively provided with positioning pins to prevent the fingers from bending toward an opposite direction, and to limit a maximum bending angle of each of the segments toward the palm to 90 degrees.

14. The under-driven prosthetic hand with a self-adaptive grasping function according to claim 4, wherein each of the metacarpophalangeal segments and the middle segments of the respective fingers are all respectively provided with positioning pins to prevent the fingers from bending toward an opposite direction, and to limit a maximum bending angle of each of the segments toward the palm to 90 degrees.

15. The under-driven prosthetic hand with a self-adaptive grasping function according to claim 5, wherein each of the metacarpophalangeal segments and the middle segments of the respective fingers are all respectively provided with positioning pins to prevent the fingers from bending toward an opposite direction, and to limit a maximum bending angle of each of the segments toward the palm to 90 degrees.

* * * * *